United States Patent [19]
Graham et al.

[11] Patent Number: 5,986,071
[45] Date of Patent: Nov. 16, 1999

[54] METHOD FOR C-TERMINAL DEGRADATION OF PEPTIDES AND PROTEINS

[75] Inventors: Kenneth S. Graham, Sierra Madre; John E. Shively, Arcadia, both of Calif.

[73] Assignee: City of Hope, Duarte, Calif.

[21] Appl. No.: 08/876,320

[22] Filed: Jun. 16, 1997

[51] Int. Cl.⁶ .............................. A61K 38/01; C07K 1/00; G01N 33/00

[52] U.S. Cl. ......................... 530/407; 530/408; 530/409; 436/89

[58] Field of Search .............................. 436/89; 530/402, 530/407, 408, 409, 410, 810, 815

[56] References Cited

U.S. PATENT DOCUMENTS 5,059,540  10/1991  Bailey ........................................ 436/89
5,432,092  7/1995   Bailey et al. .............................. 436/89

OTHER PUBLICATIONS

Solomans, T. "Organic Chemistry", 2nd edition (1980) (Wiley: New York) pp. 187–191.
Carey et al. "Advanced Organic Chemistry", 2nd edition (1984) (Plenum Press: New York) pp. 263–271.
Streitwieser et al. "Introduction to Organic Chemistry", 2nd edition, (1981) (Macmillan: New York) pp. 164–170.
Sayre, L. "Metal ion catalysis of amide hydrolysis," J. Am. Chem. Soc. (1986) 108: 1632–35.
Fersht, A. "Acyl–transfer of amides and esters with alcohols and thiols. A reference system for the serine and cysteine proteinases. Concerning the N protonation of amides and amide–imidate equilibria," J. Am. Chem. Soc. (1971) 93(14): 3504–15.

*Primary Examiner*—Jon P. Weber
*Assistant Examiner*—Susan Hanley
*Attorney, Agent, or Firm*—Rothwell Figg Ernst & Kurz

[57] ABSTRACT

A method for C-Terminal degradation of peptides and proteins involves forming a thiohydantoin derivative of the C-Terminal amino acid and then cleaving the derivatized amino acid by reaction with methoxide or methiolate ions.

23 Claims, 15 Drawing Sheets

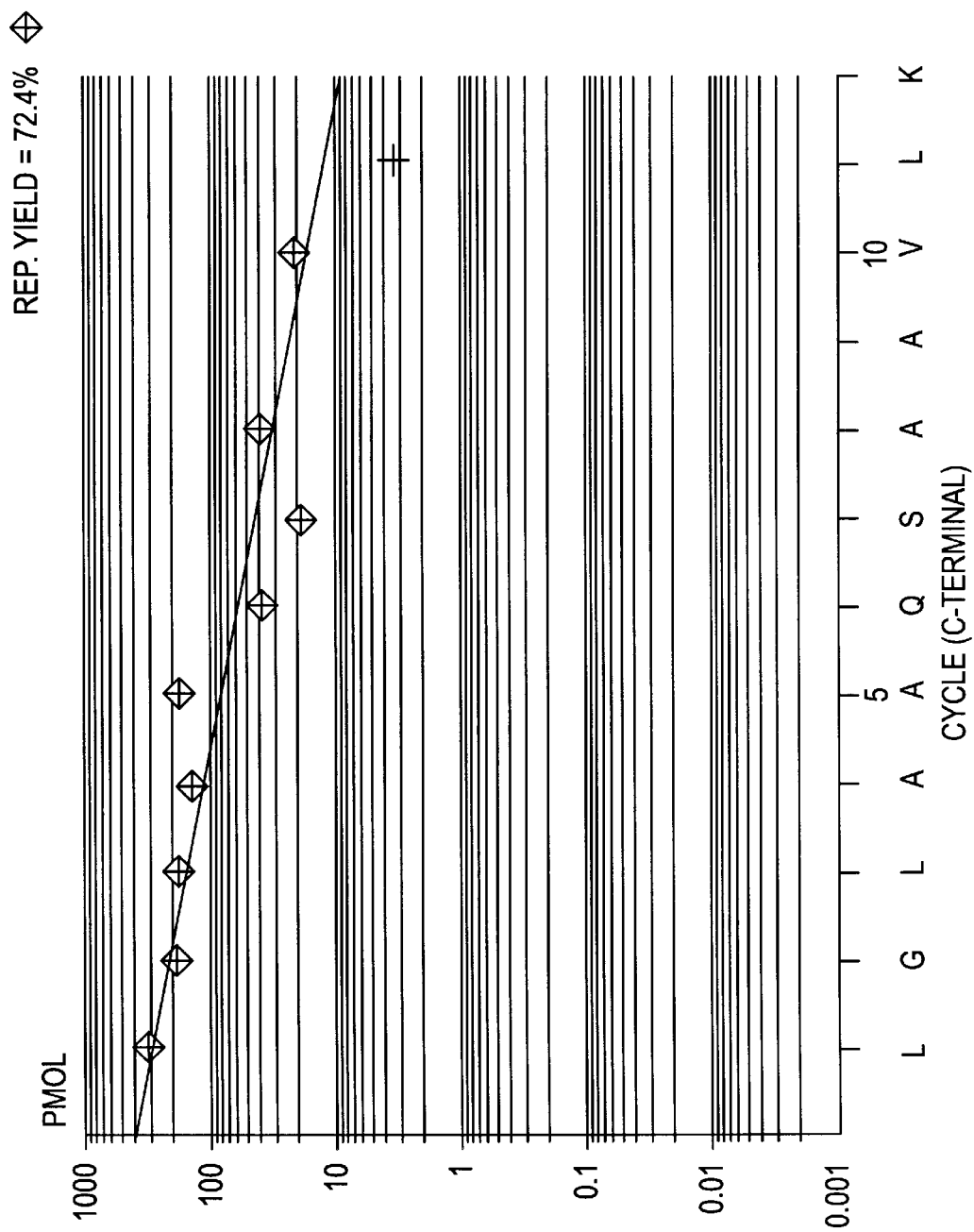

METHOD FOR C-TERMINAL DEGRADATION OF PEPTIDES AND PROTEINS

This invention was funded in part by the National Institutes of Health under Grant No. RO1-GM46022. The U.S. Government may have certain rights in the invention

BACKGROUND OF THE INVENTION

1. Field of the Invention

The present invention relates to a method for the C-terminal degradation of peptides and proteins. More particularly, the invention relates to an efficient method of cleaving a C-terminal thiohydantoin amino acid from a derivatized peptide or protein. The method allows regeneration of the carboxy terminus on the shortened peptide and is effective for multiple reaction cycles. The method results in the production of a hydantoin derivative of the cleaved amino acid which can be detected, e.g., by HPLC. Thus, the method is useful in C-terminal sequencing, as well as other procedures in which controlled degradation from the C-terminus is desired.

2. Background

U.S. Pat. No. 5,059,540, which was issued to Jerome M. Bailey on Oct. 22, 1991 (incorporated herein by reference), traces the development of methods for the sequential degradation of peptides and proteins from the carboxy terminus and contains a review of pertinent literature. That patent describes the use of (1) alkali metal salts of lower trialkylsilanols and (2) trialkylamine-N-oxides as reagents for cleaving C-terminal thiohydantoin amino acids from derivatized peptides and proteins.

While the use of trimethylsilanolate in alcohol has become a preferred method for sequential cleavage of C-terminal amino acids, it nevertheless suffers from certain disadvantages. For example, this reagent is not suitable for an extended number of degradation cycles. Moreover, the method is attended by problems when used in automated sequencing machines, as a result of the formation of precipitates that can clog valves and lines.

Accordingly, a need still exists for an efficient method of cleaving a C-terminal thiohydantoin amino acid from a derivatized peptide or protein.

SUMMARY OF THE INVENTION

In accordance with the present invention, a method for cleaving a C-terminal amino acid from a peptide or protein comprises converting the C-terminal amino acid to a thiohydantoin amino acid derivative and cleaving the thiohydantoin amino acid derivative from the peptide or protein with lower alkoxide, lower alkylthiolate or lower alkyl selenide ions to produce a thiohydantoin derivative of the amino acid previously at the C-terminus and a peptide or protein lacking such amino acid.

BRIEF DESCRIPTION OF THE DRAWINGS

The invention is illustrated by reference to the accompanying drawings in which.

FIG. 10 is a repetitive yield plot for the sequential degradations illustrated in FIGS. 9(A)–9(E).

DETAILED DESCRIPTION OF THE INVENTION

Figures 1A, 1B:
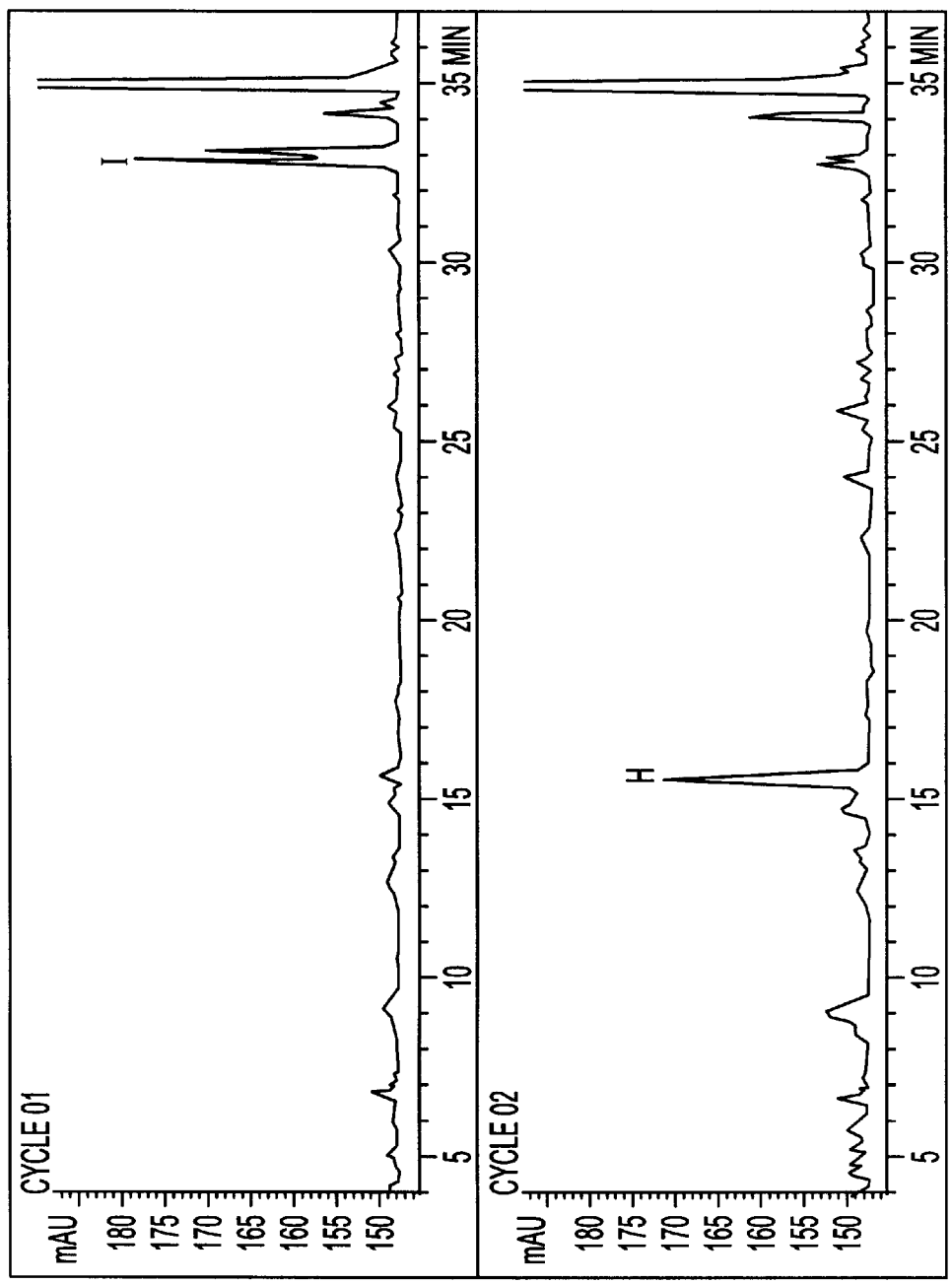
FIGS. 1(A)–1(D) show reverse phase high performance liquid chromatograms ("HPLC") depicting the analysis of the products from the first 4 cycles of sequential C-terminal degradation of β-lactoglobulin.
Figures 1C, 1D:
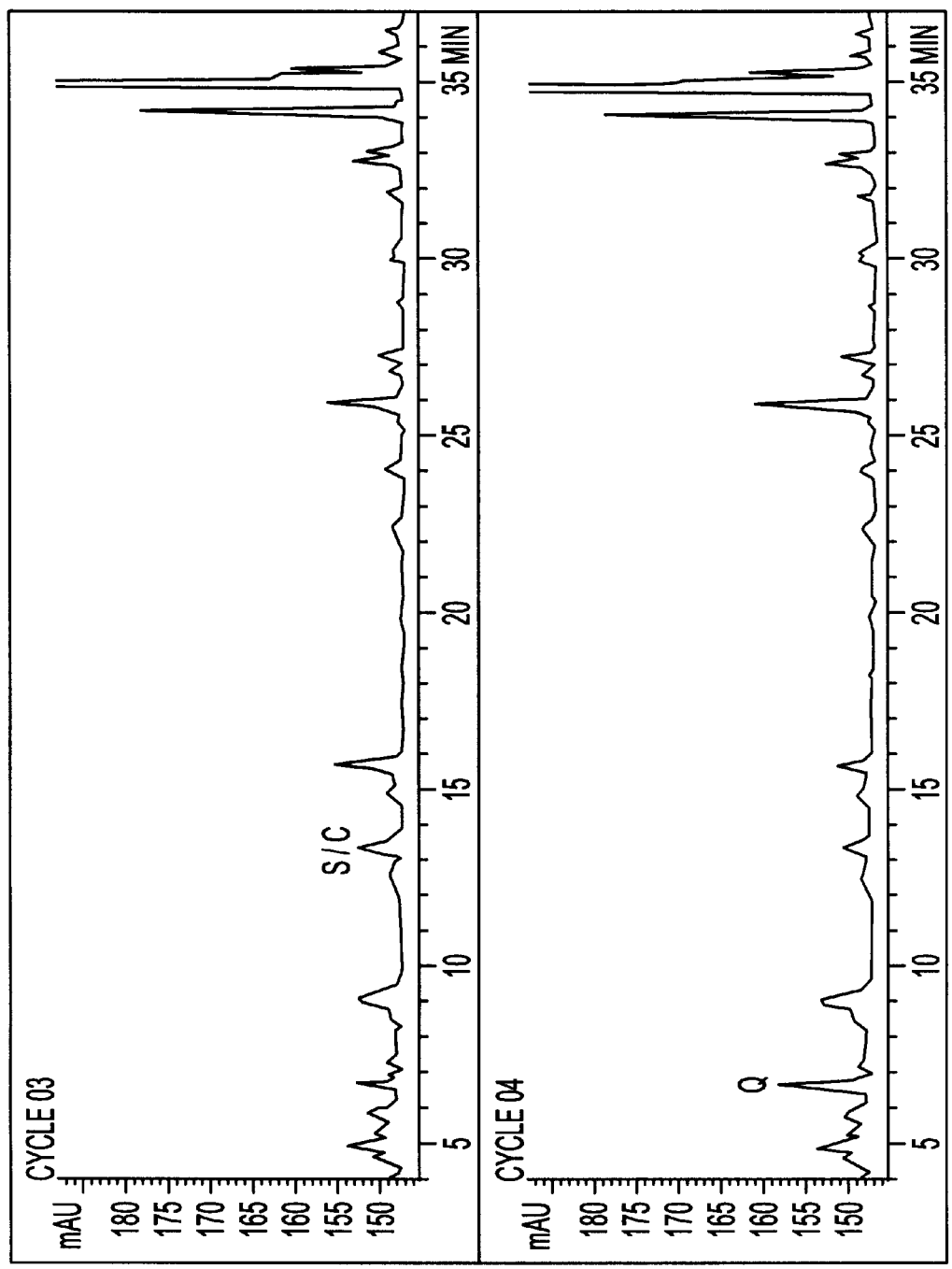

The method of this invention employs lower alkoxide, lower alkyl thiolate or lower alkyl selenide ions for the cleavage of a thiohydantoin derivatized C-terminal amino acid from a peptide or protein. The C-terminal amino acid may be converted to the thiohydantoin derivative by known procedures. A preferred procedure involves reacting the peptide or protein with diphenylphosphorylisothiocyanate in benzene, followed by cyclization in pyridine. An alternative procedure involves the use of acetic anhydride and trimethylsilylisothiocyanate ("TMS-ITC") as described in U.S. Pat. No. 5,059,540. Also see Hawke, D. H., et al. *Anal. Biochem.*, 166: 298–307 (1987) and Hawke, D. H., U.S. Pat. No. 4,837,165.

The cleavage of the C-terminal thiohydantoin amino acid, according to this invention (using a tripeptide for illustration), may be represented by the following formula:

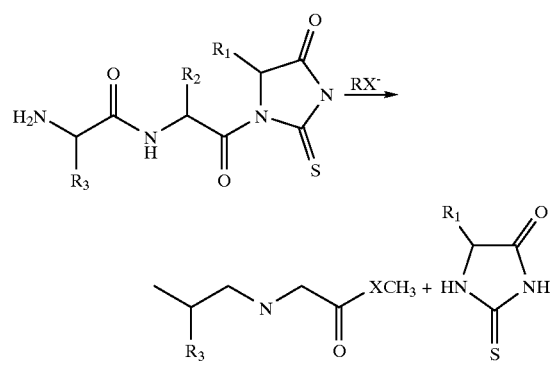

wherein $R_1$, $R_2$ and $R_3$ are characteristic side chains of the amino acids, and X is oxygen, sulfur or selenium. R is preferably methyl or ethyl, most preferably methyl. X is preferably oxygen or sulfur. Thus particularity preferred cleavage reagents are methoxide and methiolate.

The counterion for the cleavage reagent is advantageously an alkali metal, alkaline earth metal, ammonium ion or the like. Preferably, the cleavage reagent is in the form of sodium, lithium, potassium or cesium salt. Preliminary studies have indicated that, when methoxide ions are used as the cleaving agent, reaction yields are affected by the counterion in the following order: Cs>K>Na>Li. However, other studies indicate that the counterion also affects the number of successive degradation cycles to which the peptide or protein may be subjected. The counterion affects the number of cycles in the following order: Na>K>Cs. Thus it appears that by selecting the counterion, an optimal balance between initial yield and number of cycles can be obtained. Lithium may be a preferred counterion for most applications.

The cleavage reaction may be conducted in any solvent that does not adversely affect the reactants or interfere with the cleavage reaction. It is preferred to conduct the reaction in a solvent or solvent system having a dielectric constant of from about 15 to about 35, preferably from about 21 to about 25. Solvents that have been found to be effective include methanol, ethanol and mixtures thereof or mixtures thereof with butanol, e.g., 1:1 v/v methanol-t-butanol.

The peptide or protein is advantageously immobilized on a solid support to facilitate separation of the cleaved thiohydantoin amino acid derivative from the resulting peptide or protein residue. When methoxide is used as the cleavage reagent, the peptide or protein is advantageously immobilized on a polytetrafluoroethylene ("PTFE") membrane, e.g., a Teflon® or Zitex® (porous PTFE) membrane. Methiolate salts are less basic and thus may be used with conventional polyvinylidenedifluoride ("PVDF") membranes.

The cleavage reagent is employed at a concentration that provides efficient and effective cleavage, while keeping unwanted side reactions within tolerable limits. The cleavage reagents are generally employed at concentrations ranging from about 0.05M to about 0.5M, methoxide salts are preferably employed at concentrations from about 0.11M to about 0.33M, most preferably from about 0.18M to about 0.24M. Methiolate salts are preferably used at concentrations ranging from about 0.11M to about 0.25M, most preferably from about 0.14M to about 0.18M.

The cleavage reaction advantageously is conducted at ambient to elevated temperatures, e.g., from about room temperature to about 50° C., preferably from about 30° C. to about 45° C. While it is preferred to minimize the amount of water in the system because it consumes reagents, water is not otherwise detrimental. Therefore the conditions need not be strictly anhydrous. The reaction is permitted to proceed until the C-terminal thiohydantoin amino acid is cleaved from substantially all of the protein or peptide molecules.

Following the cleavage reaction, the solution containing the cleaved thiohydantoin amino acid derivative may be applied to a high-performance liquid chromatography ("HPLC") column using conventional procedures, such as, for example, those described in U.S. Pat. No. 5,059,540. The cleavage reagents employed in this invention do not absorb UV light and, therefore, do not interfere with conventional HPLC detectors.

The cleavage reaction method is well suited to peptide and protein C-terminal sequencing, particularly in automated sequencing machines. The carboxy terminus of the peptide or protein residue may readily be regenerated following cleavage. Once the carboxy terminus is reestablished, the next cleavage cycle may be performed. The novel cleavage reagents used in this invention do not cause the formation of precipitates, nor do they react significantly with the peptide or protein substrate. It has been found that in excess of five cycles, preferably in excess of ten cycles, can be performed (up to 15 cycles have been demonstrated for methiolate)

This invention is further illustrated by the following examples, which are not intended to limit the invention.

EXAMPLES 1–5

These examples describe the C-terminal sequencing of β-lactoglobulin and horse apomyoglobin using both methoxide and methiolate cleavage reagents and of human serum albumin using a methiolate cleavage reagent. The general procedures, reagents and equipment used for thiohydantoin formation and cleavage are described below. The results are shown in FIGS. 1–10.

Thiohydantoin Formation

The reactions described in these examples were performed using a Hewlett Packard HP G1009A automated sequencer. In this instrument the protein was immobilized on a porous PTFE (Zitex®) membrane which was placed in a temperature controlled reaction vessel. All derivatizations, washes and reactions were performed by timed deliveries of solvents and reagents to the reaction vessel. The basic automated program used for thiohydantoin formation was Hewlett Packard's Method 2.0. The reagents used are shown in Table 1 and the steps and conditions for thiohydantoin formation are described in Table 2. After the proteinyl thiohydantoin was formed the sample in the reaction vessel was rinsed with 5R followed by rinsing with 2R. The sample was then dried, neutralized with 4R, rinsed with 2R and dried again. At this point the proteinyl thiohydantoin was ready for cleavage.

TABLE 1

Composition of Reagents and Solvents

| | |
|---|---|
| 1R | 1.0 M Diphenylphosphorylisothiocyanate in Benzene |
| 2R | 2.0% (v/v) Pyridine/Heptane |
| 3R | Cleavage Agent |
| 4R | Hewlett Packard reagent DIEA, Water, EthylAcetate, Acetonitrile |
| 5R | Trifluoroacetic Acid |
| 1S | Acetonitrile |
| 2S | Acetonitrile |

Thiohydantoin Cleavage

Cleavage of the thiohydantoin from the protein was accomplished by delivering 30 ul of a solution containing either 0.165M sodium methiolate or 0.22M sodium methoxide to the reaction vessel containing the sample. The methoxide or methiolate was dissolved in either absolute ethanol or 1:1 (v/v) t-butanol:methanol. The cleavage agent was allowed to react with the peptidyl thiohydantoin for 30 sec at 40° C. The solution was then transferred from the reaction vessel into a conversion flask. The sample was rinsed with 2 S and the 2 S rinse was transferred into the conversion flask. The sample was then dried with an argon flush and the cleavage protocol described above was repeated a second time. After the second round cleavage the material in the conversion flask was concentrated by evaporating the solvent under a stream of argon at 50° C. The residue was dissolved in the appropriate HPLC solvent and injected into an HPLC system, containing a reverse phase column, to determine which thiohydantoin derivative was formed. The resulting HPLC chromatograms are shown in FIGS. 1(A)–1(D), 3(A)–3(E), 5(A)–5(D), 7(A)–7(E) and 9(A)–9(E). The yields of the derivatized amino acids in repetitive cycles of degradation were determined, and the repetitive yield plots are shown in FIGS. 2, 4, 6, 8 and 10.

TABLE 2

Basic Conditions Used for Thiohydantoin Formation

| Step | Time (sec) | Temperature in centigrade |
|---|---|---|
| Dry reaction vessel with Argon flush | 100 | 60 |
| 5R rinse | 95 | 60 |
| 1S rinse | 15 | 80 |
| Dry reaction vessel with Argon flush | 60 | 80 |
| 2S rinse | 24 | 80 |
| Dry reaction vessel with Argon flush | 10 | 80 |
| 1R coupling | 125 | 80 |
| Dry reaction vessel with Argon flush | 10 | 80 |
| 2S rinse | 24 | 80 |
| Dry reaction vessel with Argon flush | 10 | 80 |
| 2R thiohydantoin cyclization | 15 | 80 |
| Dry reaction vessel with Argon flush | 10 | 80 |
| 2S rinse | 24 | 80 |
| Dry reaction vessel with Argon flush | 10 | 80 |
| 1R coupling | 125 | 80 |
| Dry reaction vessel with Argon flush | 10 | 80 |
| 2S rinse | 24 | 80 |
| Dry reaction vessel with Argon flush | 10 | 80 |
| 2R thiohydantoin cyclization | 15 | 80 |
| Dry reaction vessel with Argon flush | 10 | 80 |
| 2S rinse | 24 | 80 |
| Dry reaction vessel with Argon flush | 10 | 80 |
| 1R coupling | 125 | 80 |
| Dry reaction vessel with Argon flush | 10 | 80 |
| 2S rinse | 24 | 80 |
| Dry reaction vessel with Argon flush | 10 | 80 |
| 2R thiohydantoin cycization | 15 | 80 |
| Dry reaction vessel with Argon flush | 10 | 80 |
| 2S rinse | 24 | 80 |
| Dry reaction vessel with Argon flush | 10 | 80 |

Example 1

FIGS. 1(A)–1(D) show the reverse phase chromatograms depicting the analysis of the products from the first 4 cycles of sequential C-terminal degradation of β-lactoglobulin. The cleavage reagent was 0.22M sodium methoxide dissolved in 1:1 t-butanol:methanol. In cycle 01 the thiohydantoin generated was the isoleucine derivative indicated by (I) on the chromatogram. In cycle 02 the thiohydantoin generated was the histidine derivative indicated by (H) on the chromatogram. In cycle 03 the thiohydantoin generated was the serine/cystine derivative indicated by (S/C) on the chromatogram. In cycle 04 the thiohydantoin generated was the glutamate derivative indicated by (Q) on the chromatogram.

Figure 2:
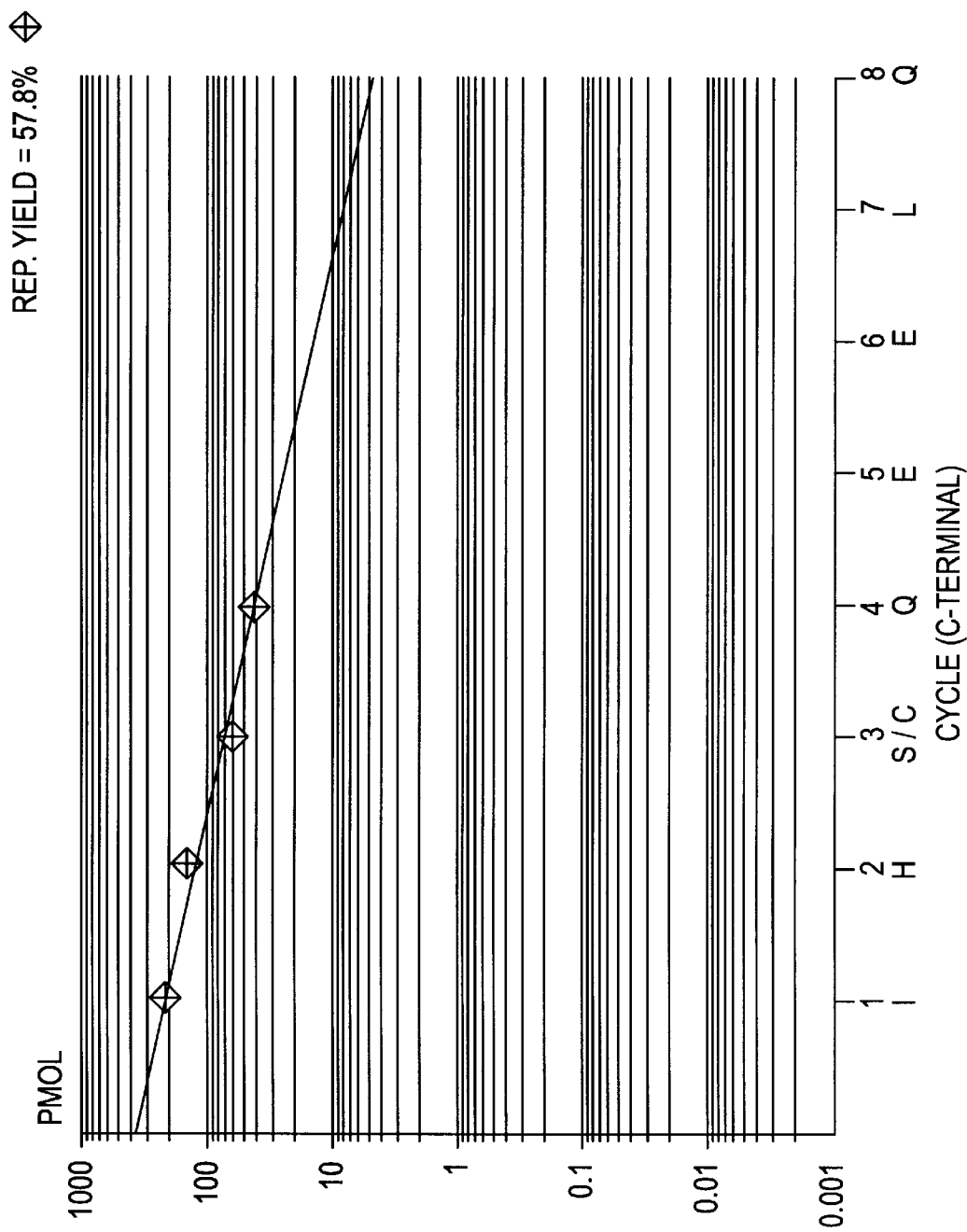
FIG. 2 is a repetitive yield plot for the sequential degradations illustrated in FIGS. 1(A)–1(D).
Figures 3A, 3B, 3C:
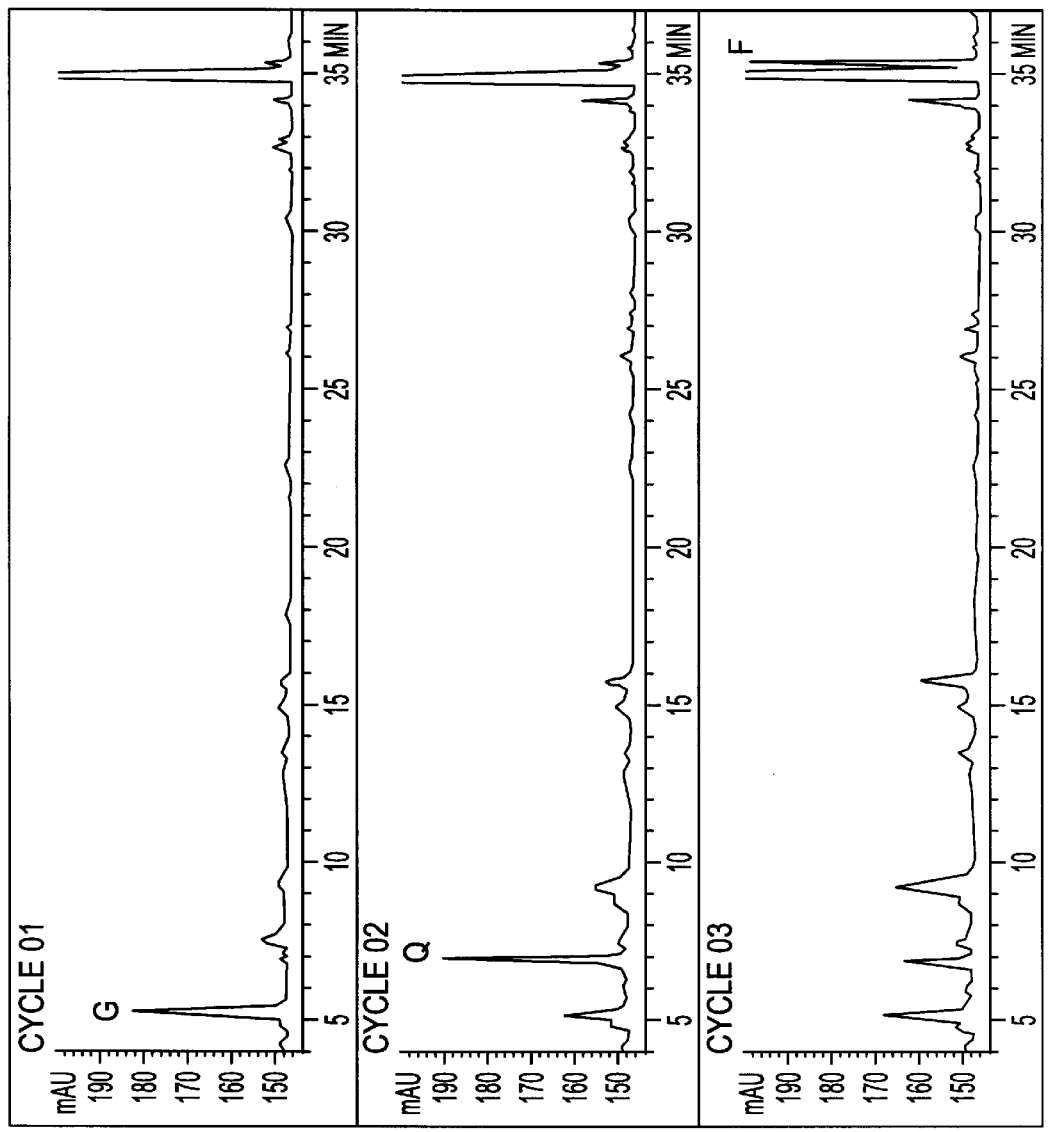
FIGS. 3(A)–3(E) show reverse phase HPLC's depicting the analysis of the first 5 cycles of sequential C-terminal degradation of horse apomyoglobin.
Figures 3D, 3E:
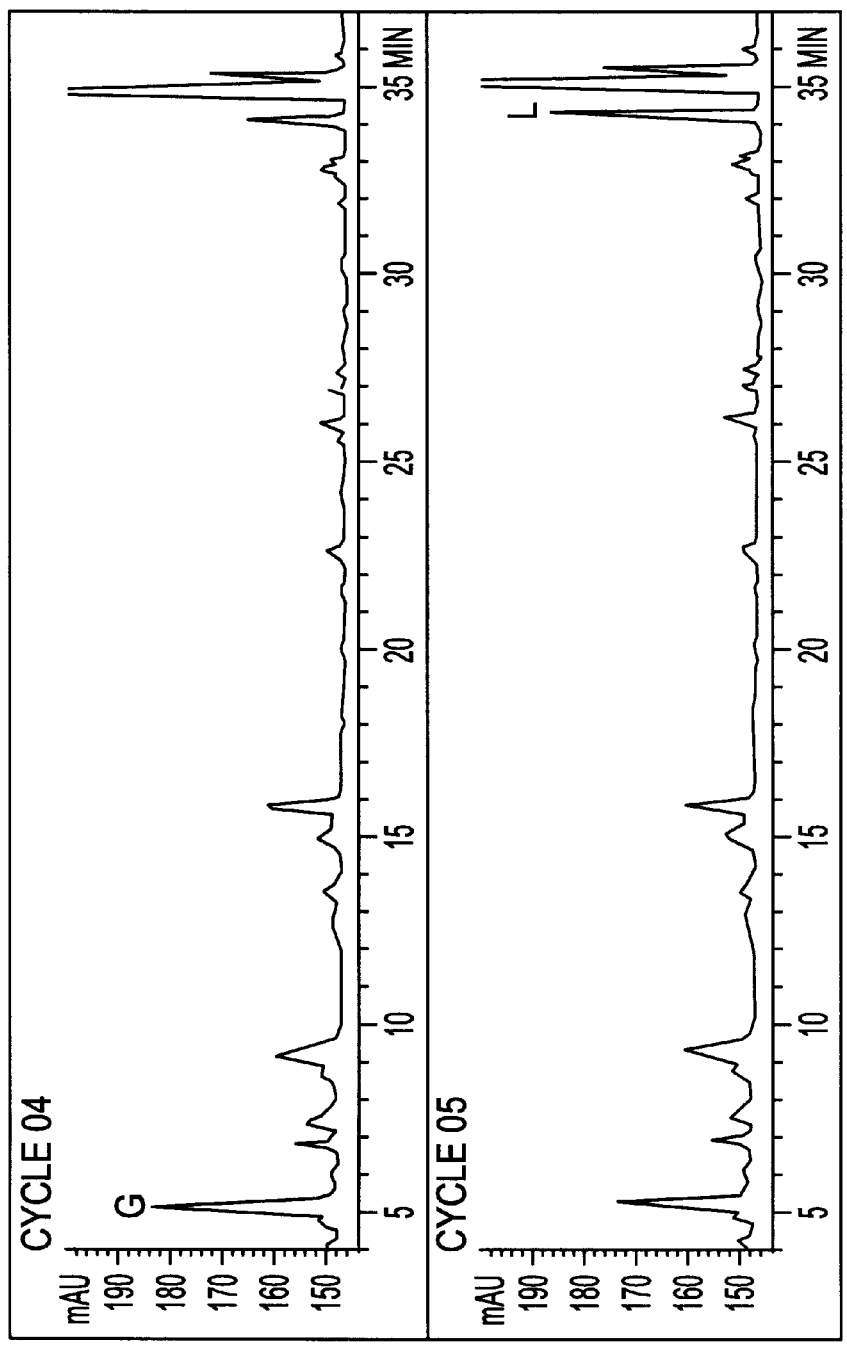

FIG. 2 shows the C-terminal repetitive yield plot for the sequential C-terminal degradation of β-lactoglobulin illustrated in FIGS. 1(A)–1(D). The plot shows a repetitive yield of 57.6% and that sequence information was obtained for 4 cycles.

Example 2

FIGs. 3(A)–3(E) shows the reverse phase chromatograms depicting the analysis of the products from the first 5 cycles of sequential C-terminal degradation of horse apomyoglobin. The cleavage agent was 0.22M sodium methoxide dissolved in 1:1 t-butanol:methanol. In cycle 01 the thiohydantoin generated was the glycine derivative indicated by (G) on the chromatogram. In cycle 02 the thiohydantoin generated was the glutamine derivative indicated by (Q) on the chromatogram. In cycle 03 the thiohydantoin generated was the phenylalanine derivative indicated by (F) on the chromatogram. In cycle 04 the thiohydantoin generated was the glycine derivative indicated by (G) on the chromatogram. In cycle 05 the thiohydantoin generated was the leucine derivative indicated by (L) on the chromatogram.

Figure 4:
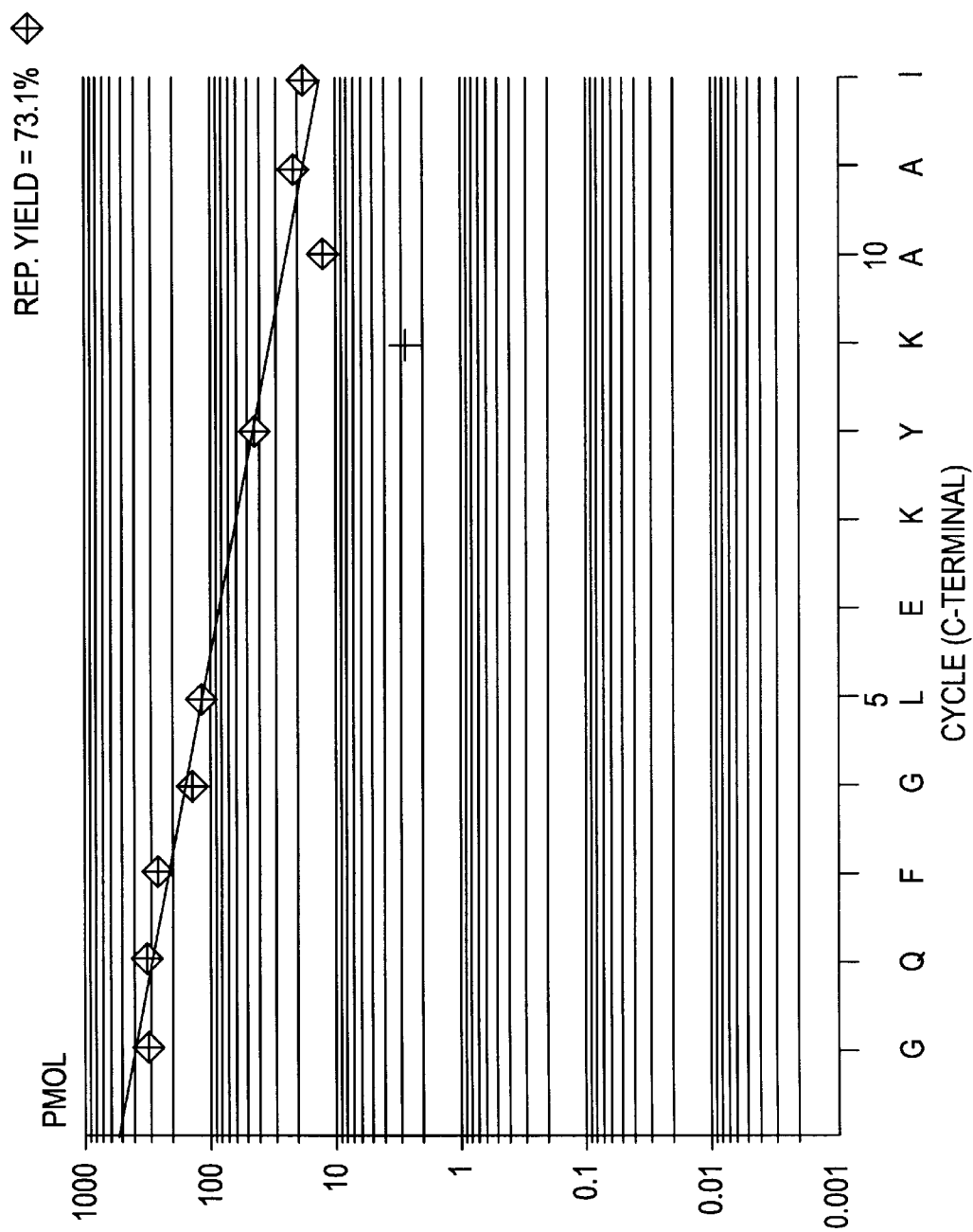
FIG. 4 is a repetitive yield plot for the sequential degradations illustrated in FIGS. 3(A)–3(E).
Figures 5A, 5B:
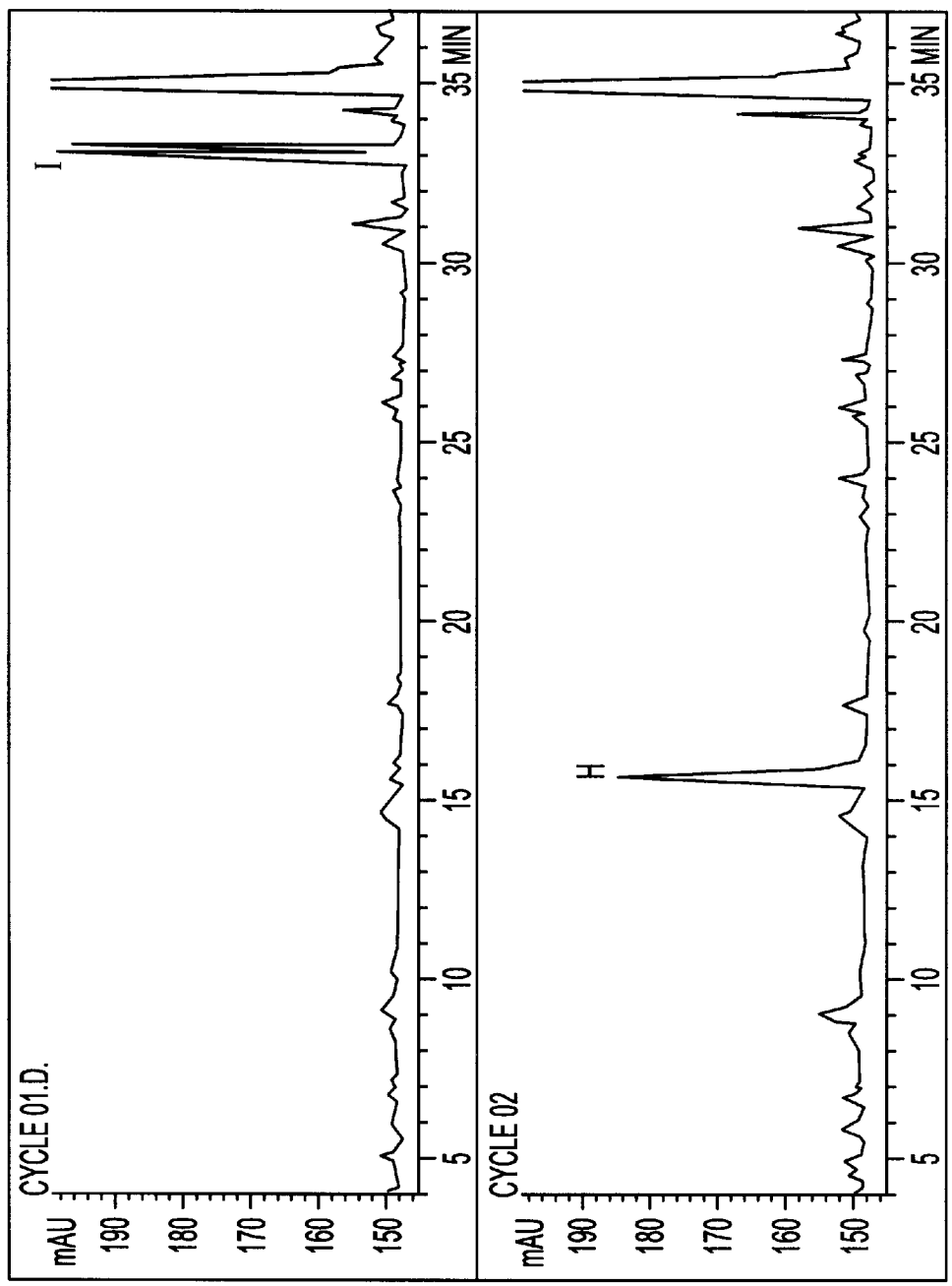
FIGS. 5(A)–5(D) show reverse phase HPLC's depicting the analysis of the products from the first 4 cycles of sequential C-terminal degradation of β-lactoglobulin using conditions different from those employed in the reactions illustrated in FIGS. 1(A)–1(D).
Figures 5C, 5D:
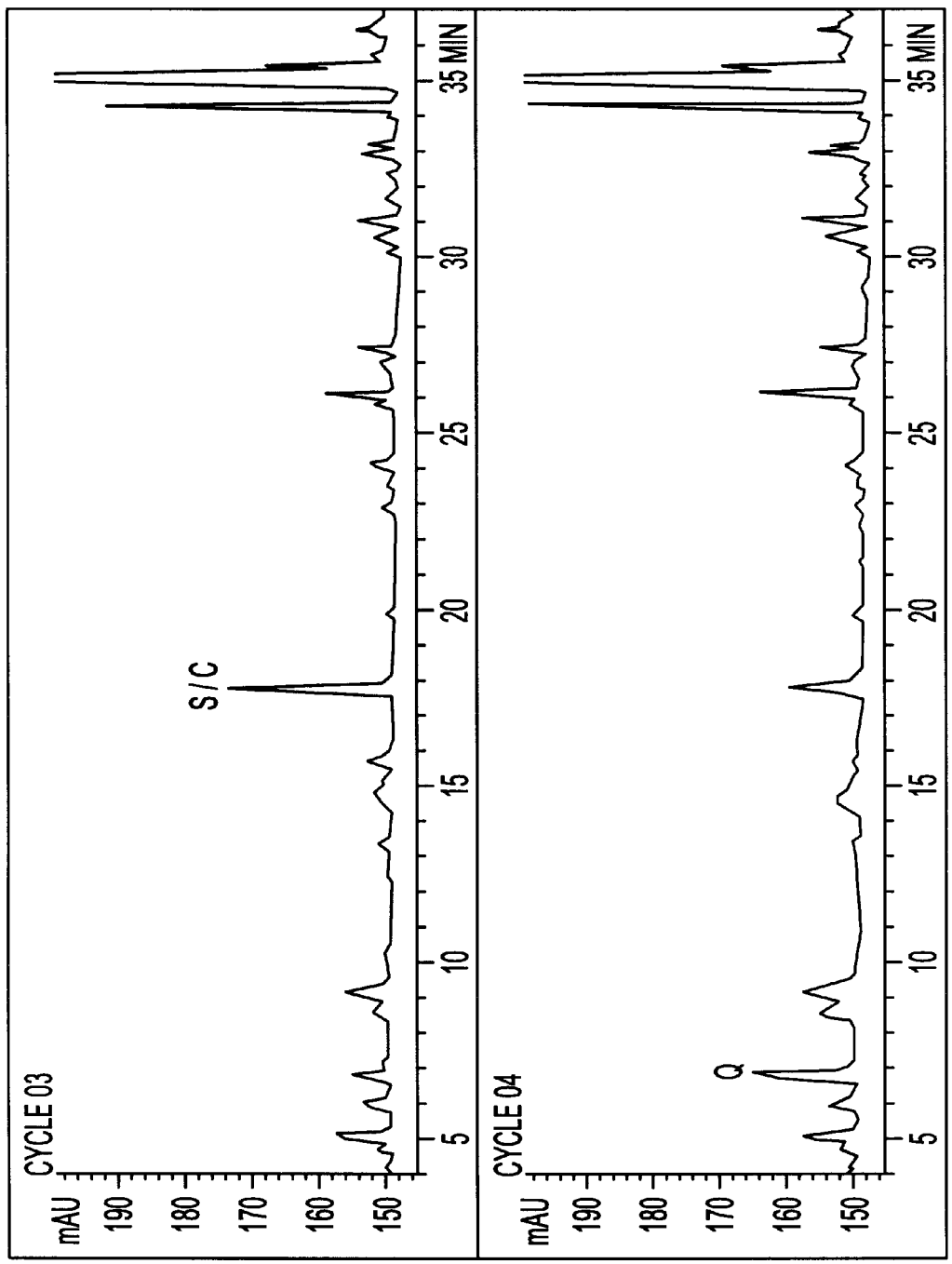

FIG. 4 shows the C-terminal repetitive yield plot for the sequential C-terminal degradation of horse apomyoglobin illustrated in FIGS. 3(A)–3(E). The plot shows a repetitive yield of 73.1% and that sequence information was obtained for 12 cycles.

Example 3

FIGS. 5(A)–5(D) show the reverse phase chromatograms depicting the analysis of the products from the first 4 cycles of sequential C-terminal degradation of β-lactoglobulin. The cleavage agent was 0.165M sodium methiolate dissolved in absolute ethanol. In cycle 01 the thiohydantoin generated was the isoleucine derivative indicated by (I) on the chromatogram. In cycle 02 the thiohydantoin generated was the histidine derivative indicated by (H) on the chromatogram. In cycle 03 the thiohydantoin generated was the serine/cystine derivative indicated by (S/C) on the chromatogram. In cycle 04 the thiodydantoin generated was the glutamate derivative indicated by (Q) on the chromatogram.

Figure 6:
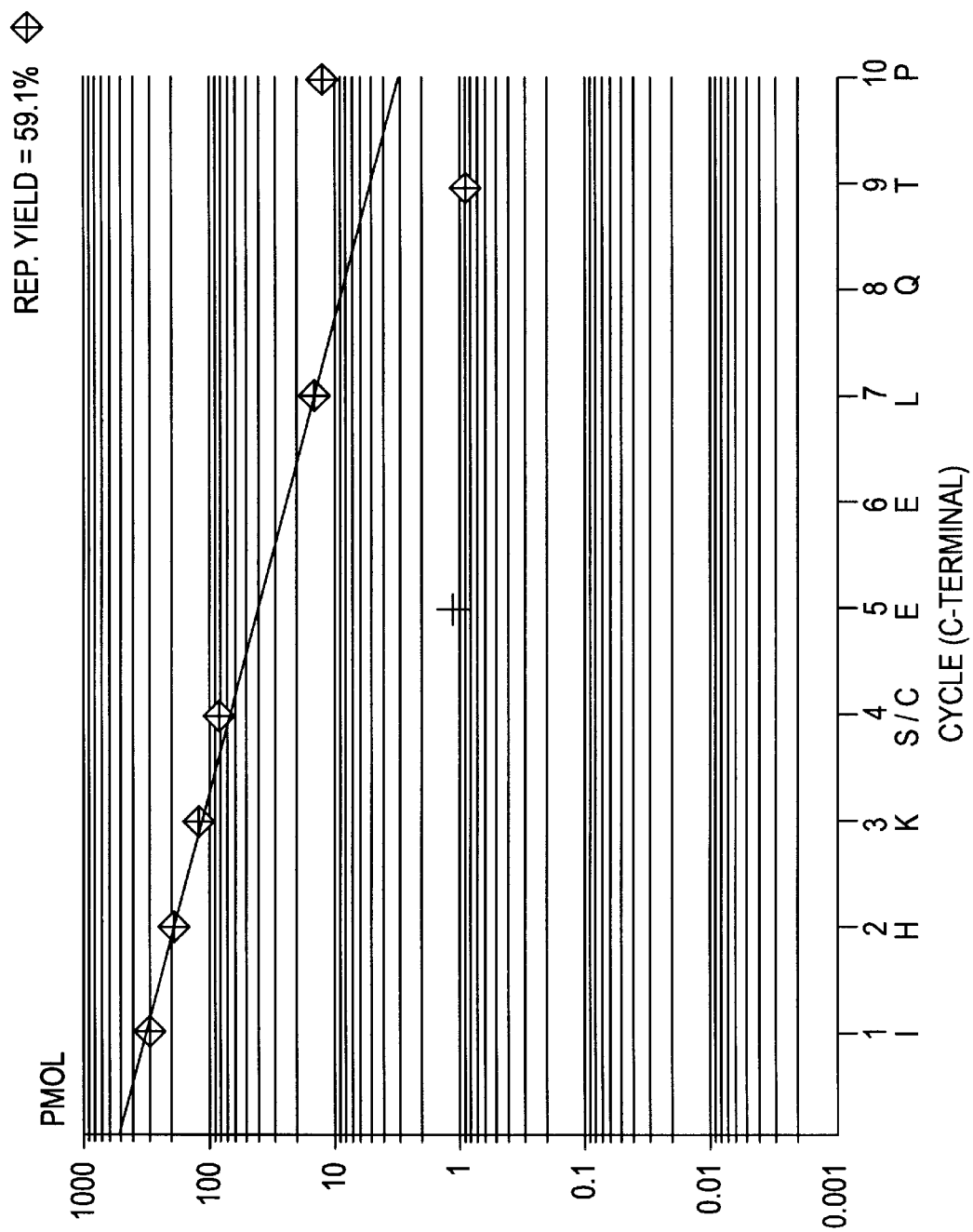
FIG. 6 is a repetitive yield plot for the sequential degradations illustrated in FIGS. 5(A)–(D).
Figures 7A, 7B, 7C:
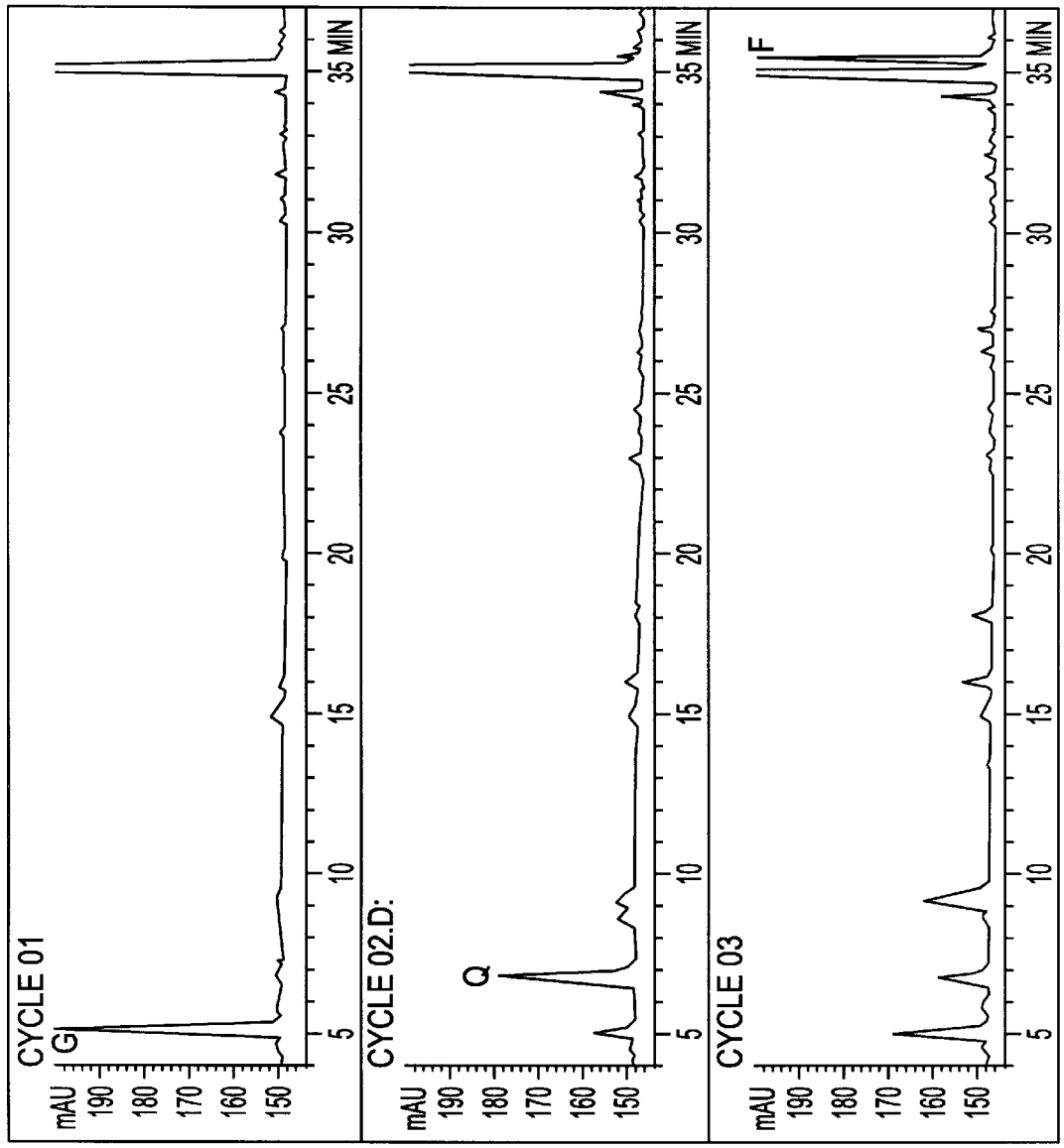
FIGS. 7(A)–7(E) show reverse phase HPLC's depicting the first 5 cycles of sequential C-terminal degradation of horse apomyoglobin using conditions different from those employed in the reactions illustrated in FIG. 2.
Figures 7D, 7E:
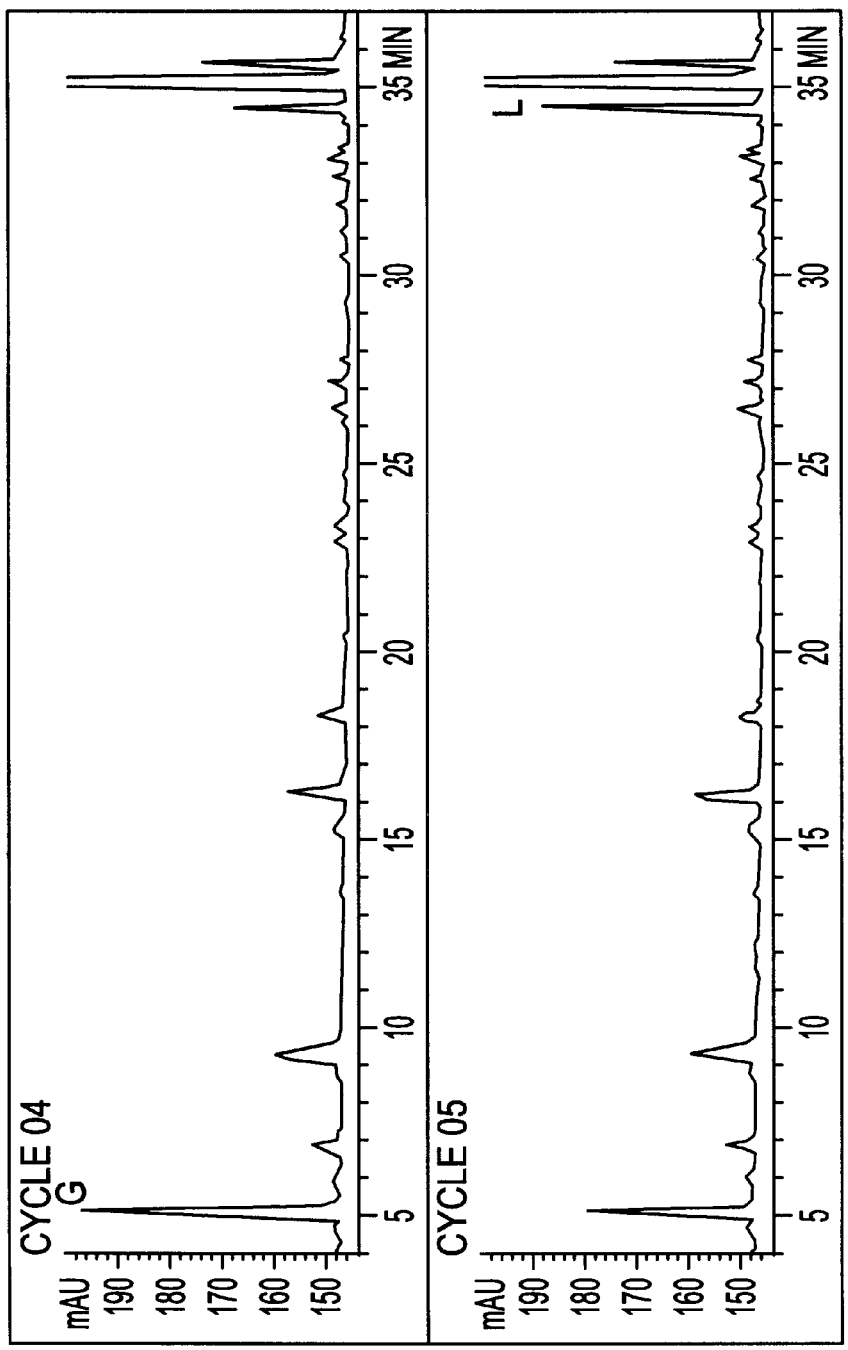

FIG. 6 shows the C-terminal repetitive yield plot for the sequential C-terminal degradation of β-lactoglobulin illustrated in FIGS. 5(A)–5(D). The plot shows a repetitive yield of 59.1% and that sequence information was obtained for 9–10 cycles.

Example 4

FIGS. 7(A)–7(E) show the reverse phase chromatograms depicting the analysis of the products from the first 5 cycles of sequential C-terminal degradation of horse apomyoglobin. The cleavage agent was 0.165M sodium methiolate dissolved in absolute ethanol. In cycle 01 the thiohydantoin generated was the glycine derivative indicated by (G) on the chromatogram. In cycle 02 the thiohydantoin generated was the glutamine derivative indicated by (Q) o the chromatogram. In cycle 03 the thiohydantoin generated was the phenylalanine derivative indicated by (F) on the chromatogram. In cycle 04 the thiohydantoin generated was the glycine derivative indicated by (G) on the chromatogram. In cycle 05 the thiohydantoin generated was the leucine derivative indicated by (L) on the chromatogram.

Figure 8:
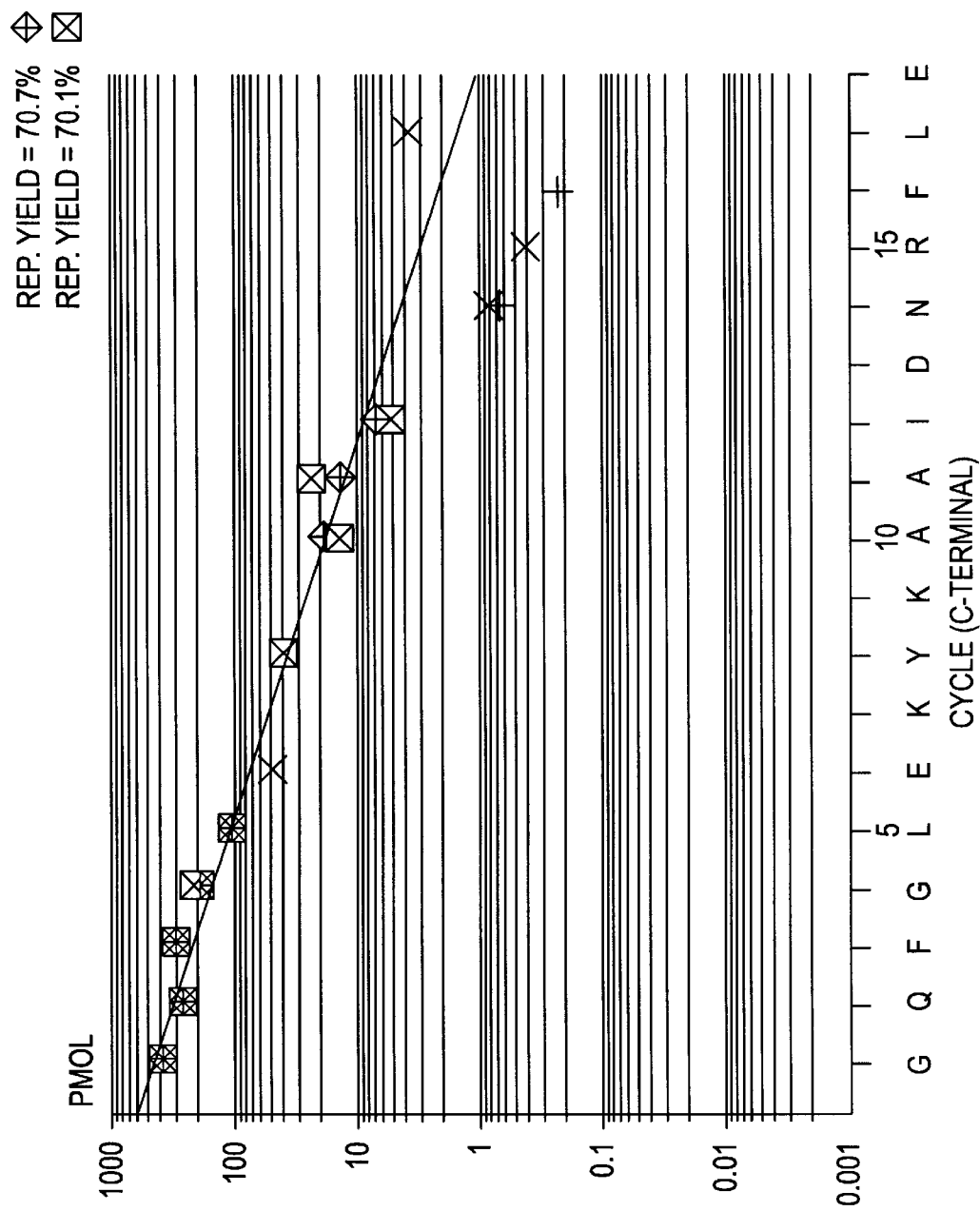
FIG. 8 is a repetitive yield plot for the sequential degradations illustrated in FIGS. 7(A)–7(E).
Figures 9A, 9B, 9C:
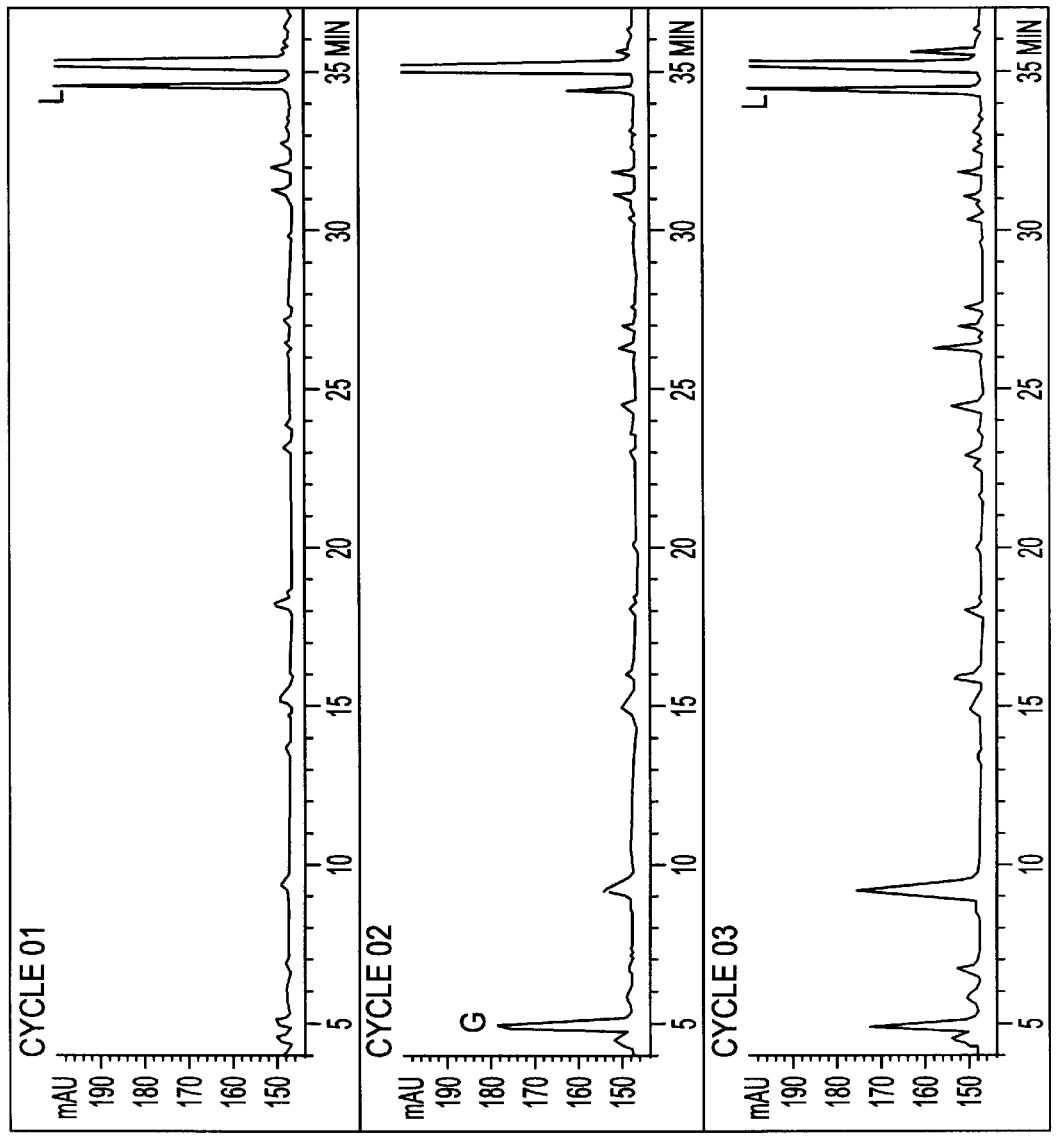
FIGS. 9(A)–9(E) show reverse phase HPLC's depicting the analysis of the products from the first 5 cycles of sequential C-terminal degradation of human serum albumin.
Figures 9D, 9E:
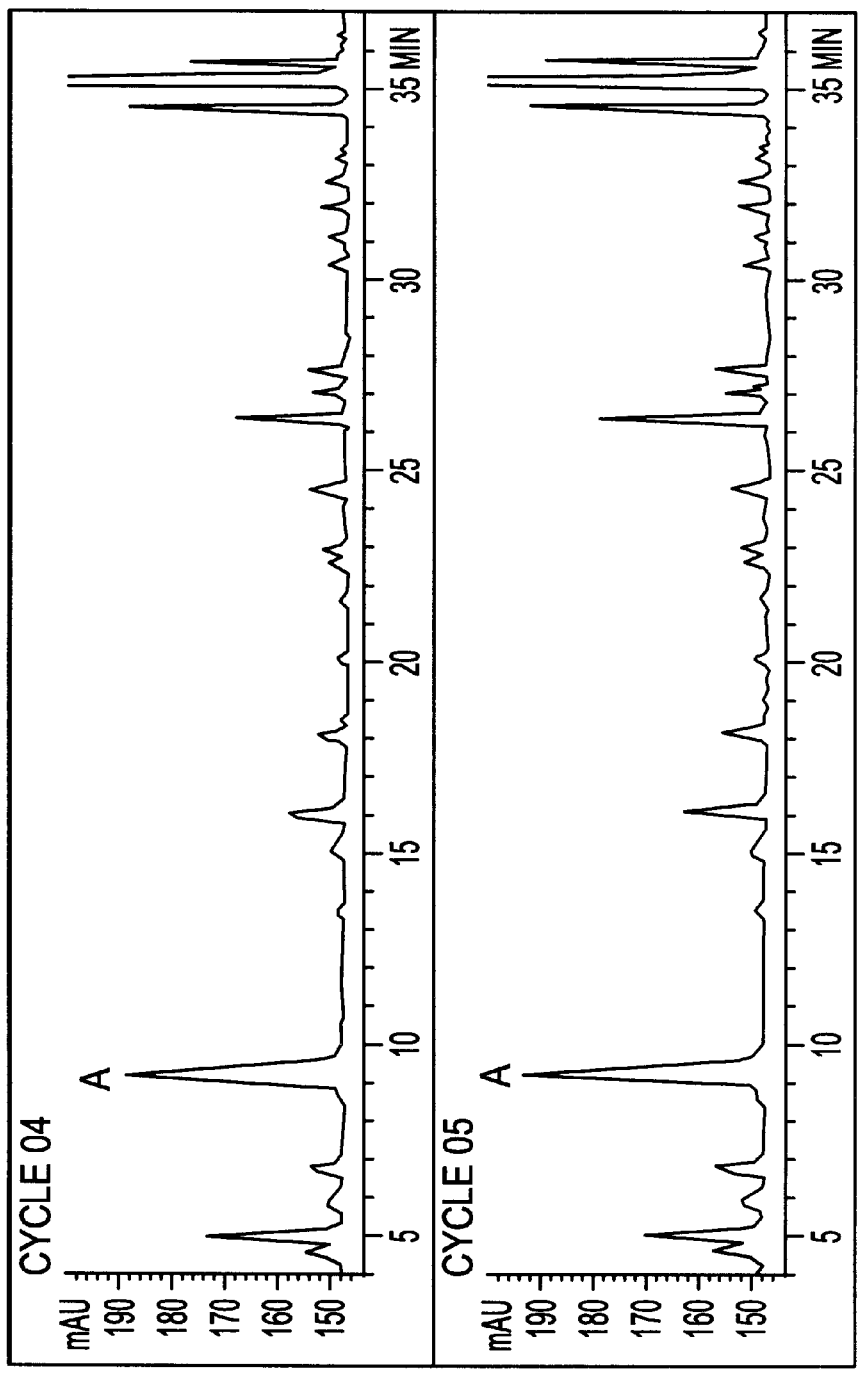

FIG. 8 shows the C-terminal repetitive yield plot for the sequential C-terminal degradation of horse apomyoglobin illustrated in FIGS. 7(A)–7(E). The plot shows an average repetitive yield of 70.4% for two apomypglobin samples. The plot also shows that sequence information was obtained for 15–17 cycles of degradation.

Example 5

FIGS. 9(A)–9(E) show the reverse phase chromatograms depicting the analysis of the products from the first 5 cycles of sequential C-terminal degradation of human serum albumin. The cleavage agent was 0.165M sodium methiolate dissolved in absolute ethanol. In cycle 01 the thiohydantoin generated was the leucine derivative indicated by (L) on the chromatogram. In cycle 02 the thiohydantoin generated was the glycine derivative indicated by (G) on the chromatogram. In cycle 03 the thiohydantoin generated was the leucine derivative indicated by (L) on the chromatogram. In cycle 04 the thiohydantoin generated was the alanine derivative indicated by (A) on the chromatogram. In cycle 05 the thiohydantoin generated is the alanine derivative indicated by (A) on the chromatogram.

FIG. 10 shows the C-terminal repetitive yield plot for the sequential C-terminal degradation of human serum albumen illustrated in FIGS. 9(A)–9(E) dissolved in absolute ethanol. The plot shows a repetitive yield of 72.4% and that sequence information was obtained for 11 cycles.

What is claimed is:

1. A method for cleaving a C-terminal amino acid from a peptide or protein, which comprises converting the C-terminal amino acid to a thiohydantoin amino acid derivative and cleaving the thiohydantoin amino acid derivative from the peptide or protein with a cleavage reagent of the formula $RX^-$ to produce a thiohydantoin derivative of the amino acid previously at the C-terminus and a peptide or protein lacking such amino acid, wherein R is lower alkyl of from 1 to about 3 carbon atoms and X is oxygen, sulfur or selenium.

2. The method of claim 1, wherein R is methyl or ethyl.

3. The method of claim 2, wherein X is oxygen or sulfur.

4. The method of claim 1, wherein the thiohydantoin amino acid derivative is cleaved from the peptide or protein with methoxide.

5. The method of claim 1, wherein the thiohydantoin amino acid derivative is cleaved from the peptide or protein with methiolate.

6. The method of claim 1, 2, 3, 4 or 5, wherein the cleavage reagent is provided to the reaction as an alkali metal, alkaline earth metal or ammonium salt.

7. The method of claim 6, wherein the methoxide or methiolate is provided to the reaction as the lithium sodium, potassium or cesium salt.

8. The method of claim 7, wherein the salt is the lithium salt.

9. The method of claim 6, wherein the methoxide or methiolate is provided to the reaction mixture in a solvent having a dielectric constant of from about 15 to about 35.

10. The method of claim 6, wherein the methoxide or methiolate is provided to the reaction mixture in a solvent having a dielectric constant of from about 21 to about 25.

11. The method of claim 9, wherein the solvent is methanol or ethanol, a mixture thereof or a mixture thereof with t-butanol.

12. The method of claim 9, wherein the concentration of the methoxide or methiolate in the solvent is from about 0.05M to about 0.5M.

13. The method of claim 9, wherein the cleavage reagent is methoxide and its concentration in the solvent is from about 0.11M to about 0.33M.

14. The method of claim 13, wherein the concentration of the methoxide in the solvent is from about 0.18 to about 0.24M.

15. The method of claim 9, wherein the cleavage reagent is methiolate and its concentration in the solvent is from about 0.11 to about 0.25M.

16. The method of claim 15, wherein the concentration of the methiolate in the solvent is from about 0.14 to about 0.18M.

17. The method of claim 6, wherein the peptide or protein is immobilized on a solid substrate.

18. The method of claim 5, wherein the peptide or protein is immobilized on a PVDF membrane.

19. The method of claim 17, wherein the cleavage reaction is cycled at least 5 times.

20. The method of claim 18, wherein the cleavage reaction is cycled at least 5 times.

21. The method of claim 17, wherein the cleavage reaction is cycled at least 10 times.

22. The method of claim 18, wherein the cleavage reaction is cycled at least 10 times.

23. A method of identifying an amino acid in a C-terminal peptide sequencing method, wherein the peptide is cleaved according to claim 1 and said thiohydantoin amino acid derivative is identified by HPLC analysis.

* * * * *